United States Patent [19]

Camenzind et al.

[11] Patent Number: 5,262,072
[45] Date of Patent: Nov. 16, 1993

[54] LUBRICANT COMPOSITION

[75] Inventors: Hugo Camenzind, Bern; Rolf Schumacher, Marly, both of Switzerland

[73] Assignee: Ciba-Geigy Corporation, Ardsley, N.Y.

[21] Appl. No.: 719,862

[22] Filed: Jun. 24, 1991

[30] Foreign Application Priority Data

Jun. 28, 1990 [CH] Switzerland ............... 2169/90

[51] Int. Cl.$^5$ ............... C10M 139/06; C10M 133/38
[52] U.S. Cl. ............... 252/32.7 E; 252/50; 252/42.7; 252/51.5 R; 252/400.53; 252/75
[58] Field of Search ............... 252/42.7, 32.7 E, 50, 252/51.5 R, 400.53

[56] References Cited

U.S. PATENT DOCUMENTS

| | | | |
|---|---|---|---|
| 3,351,647 | 11/1967 | Butler et al. | 260/429.9 |
| 3,634,238 | 1/1972 | Bridger | 252/26 |
| 4,409,114 | 10/1983 | Brois et al. | 252/42.7 |
| 4,504,404 | 3/1985 | Schumacher | 252/33.4 |
| 4,692,258 | 9/1987 | Rasberger et al. | 252/50 |
| 4,824,401 | 4/1989 | Franklin | 252/401 |
| 4,828,733 | 5/1989 | Farng et al. | 252/42.7 |
| 4,842,753 | 6/1989 | Mori et al. | 252/42.7 |
| 4,867,890 | 9/1989 | Colclough et al. | 252/327 |
| 5,055,211 | 8/1991 | Habeeb et al. | 252/42.7 |

FOREIGN PATENT DOCUMENTS

| | | |
|---|---|---|
| 0024146 | 2/1981 | European Pat. Off. . |
| 0376889 | 7/1990 | European Pat. Off. . |
| 8606378 | 11/1986 | PCT Int'l Appl. . |

OTHER PUBLICATIONS

Oliver et al., J. of Medicinal Chemistry No. 3 (1972).
Chem Abst. 87:33049x (1977).
Derwent abst. 90:203222/27.

Primary Examiner—Jacqueline V. Howard
Attorney, Agent, or Firm—William A. Teoli, Jr.; JoAnn Villamizar

[57] ABSTRACT

A composition comprising
a) a lubricant or a hydraulic fluid, and
b) at least one compound of general formula I

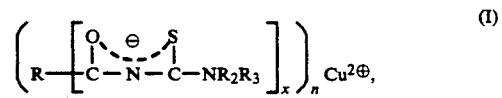

wherein x is 1 or 2 and, when x is 1, n is 2 and R has the meaning of $R_1$, or, when x is 2, n is 1 and R has the meaning of $R_4$, $R_1$ is alkyl of 1 to 25 carbon atoms, an unsubstituted or $C_1$–$C_8$-alkyl-substituted cycloalkyl group of 5 to 12 carbon atoms, alkenyl of 2 to 18 carbon atoms, phenyl, naphthyl, $C_7$–$C_{18}$phenylalkyl, $C_7$–$C_{18}$alkylphenyl or —$NR_5R_6$, and $R_2$ and $R_3$ are identical or different and are alkyl of 1–18 carbon atoms, phenyl, naphthyl, $C_7$–$C_{18}$phenylalkyl or $C_7$–$C_{18}$alkylphenyl, or $R_2$ and $R_3$, together with the linking nitrogen atom, form a 5- to 7-membered heterocyclic ring which may additionally contain a N- or O-atom, $R_4$ is alkylene of 1 to 12 carbon atoms which may be interrupted by at least one —O-group, or is alkenylene of 2 to 12 carbon atoms which may be interrupted by at least one —O-group, and $R_5$ and $R_6$ have the same meanings as $R_2$ and $R_3$. The compositions have enhanced stability to oxidative degradation.

22 Claims, No Drawings

LUBRICANT COMPOSITION

The present invention relates to novel compositions comprising a lubricant or a hydraulic fluid and, as antioxidant, at least one copper complex of an N-acylated thiourea, to the use of said copper complexes, and to a method of stabilising lubricant compositions or hydraulic fluids against oxidative or thermal degradation.

It is known in the art to treat lubricants such as mineral oils or synthetic and semisynthetic oils with additives to improve their performance properties. Particularly useful additives are those which inhibit the oxidative degradation of lubricants and ensure good storage and performance stability.

In particular, the stability requirements of modern engine oils with respect to thermal and oxidative degradation have changed as a consequence of new constructions in the field of combustion engines with self-ignition or spark-ignation. Thus, for example, the present day design and mode of operation of engines with spark-ignition give rise to the increased formation of nitrogen oxides, which in turn pass into the crankcase as blow-by gases.

Furthermore, the lubricant oil in the upper piston ring and cylinder region acts as fine sealing to the combustion chamber, where it may become contaminated with high-boiling fuel components. These given conditions are intensified by the presence of $NO_x$.

The blow-by gases, which contain increasingly higher amounts of $NO_x$, then bring about a greater susceptibility of the lubricant oil to oxidative degradation and "sludge germs" form, which ultimately lead to unwanted sludge deposits known as "black sludge".

It is assumed that this sludge formation takes the form of an $NO_x$-initiated self-oxidation of the lubricant oil.

There has been no lack of attempts to improve lubricant oils by addition of antioxidants.

It is known to add copper compounds as antioxidants to lubricants. Thus U.S. Pat. No. 3,351,647 teaches the use of phosphorus- and nitrogen-containing complexes of metals having oxidation inhibiting action, including also copper, in lubricant compositions. These complexes have a synergistic effect when used with phenyl-$\beta$-naphthylamine. Further, U.S. Pat. No. 3,634,238 discloses a combination of metals or carboxylic acid salts of metals, including also copper, with aromatic amines having a synergistic oxidation inhibiting action in organic material, especially lubricants.

A combination of dispersant, viscosity index improver, zinc dithiophosphate and copper compounds in the ppm range is disclosed in EP-A 24 146 as oxidation retarding or inhibiting system.

In addition, U.S. Pat. No. 4,828,733 discloses the use of copper salts of sterically hindered phenolcarboxylic acids as antioxidants in lubricants, and mentions a synergistic effect when using such salts with other antioxidants, such as phenolic or arylamine antioxidants.

Surprisingly, it has now been found that copper complexes of 1,1-disubstituted 3-acylthioureas are admirably suited for use as antioxidants for lubricants.

1,1-Dialkyl-3-benzoylthioureas are described by L. Beyer et al. in the Journal für praktische Chemie, Vol. 317, No. 5, 1975, pp. 829–839, as excellent chelate formers for transition metal ions such as cobalt, copper, nickel and palladium.

Further, symmetrical 3,3,3',3'-tetraalkyl-1,1-alkanediyolbis(thioureas) are known from K.-H. König et al., Chemische Berichte 120, pp. 1251–1253, (1987) as chelate ligands which are suitable for the separation and extractive enrichment of platinum metals.

Specifically, the present invention relates to a composition comprising
a) a lubricant or a hydraulic fluid, and
b) at least one compound of general formula I

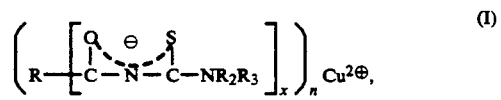

wherein x is 1 or 2 and, when x is 1, n is 2 and R has the meaning of $R_1$, or, when x is 2, n is 1 and R has the meaning of $R_4$, and $R_1$ is alkyl of 1 to 25 carbon atoms, an unsubstituted or $C_1$-$C_8$-alkyl-substituted cycloalkyl group of 5 to 12 carbon atoms, alkenyl of 2-18 carbon atoms, phenyl, naphthyl, $C_7$-$C_{18}$phenylalkyl, $C_7$-$C_{18}$alkylphenyl or —$NR_5R_6$, and $R_2$ and $R_3$ are identical or different and are alkyl of 1 to 18 carbon atoms, phenyl, naphthyl, $C_7$-$C_{18}$phenylalkyl or $C_7$-$C_{18}$alkylphenyl, or $R_2$ and $R_3$, together with the linking nitrogen atom, form a 5- to 7-membered heterocyclic ring which may additionally contain a N- or O-atom, $R_4$ is alkylene of 1 to 12 carbon atoms which may be interrupted by at least one —O-group, or is alkenylene of 2 to 12 carbon atoms which may be interrupted by at least one —O-group, and $R_5$ and $R_6$ have the same meanings as $R_2$ and $R_3$.

In the structure of formula I, the negative charge is not fixed. The formula thus encompasses the different possible resonating structures as represented typically by the following formulae:

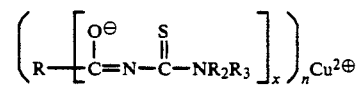

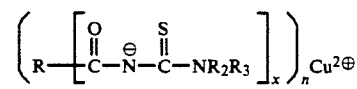

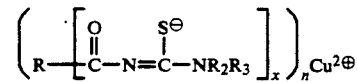

An alkyl radical $R_1$ of 1 to 25 carbon atoms may be straight-chain or branched and be typically: methyl, ethyl, propyl, isopropyl, n-butyl, isobutyl, tert-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, icosyl, henicosyl, docosyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1,1,3,3-tetramethylhexyl or 1-methylundecyl. Preferably $R_1$ is an alkyl radical of 1 to 18 carbon atoms.

Alkyl radicals may be straight-chain or branched radicals. The branched-chain radicals in particular can be in the form of mixtures of their isomers.

$R_1$ can also be alkenyl of 2 to 18 carbon atoms. Illustrative examples are vinyl, allyl, 2-methallyl, butenyl such as 2-butenyl, hexenyl such as 2-hexenyl, decenyl, undecenyl such as 10-undecenyl, heptadecenyl or oleyl.

Typical examples of the above unsubstituted or $C_1$-$C_8$alkyl-substituted cycloalkyl groups of 5 to 12 carbon atoms are cyclopentyl, cyclohexyl, cyclooctyl, cyclododecyl, 2- or 4-methylcyclohexyl, dimethylcyclohexyl, trimethylcyclohexyl, tert-butylcyclohexyl. Cyclohexyl is especially preferred.

$R_1$, $R_2$ and $R_3$ as $C_7$-$C_{18}$phenylalkyl are typically benzyl, 1- or 2-phenylethyl, 3-phenylpropyl, $\alpha,\alpha$-dimethylbenzyl, 2-phenylisopropyl, 2-phenylhexyl or benzhydryl. Benzyl is preferred.

$R_1$, $R_2$ and $R_3$ as $C_7$-$C_{18}$alkylphenyl may contain linear or branched alkyl groups, the number of said alkyl groups being 1 to 3, preferably 1 or 2. Illustrative examples are tolyl, ethylphenyl, isopropylphenyl, tert-butylphenyl, sec-pentylphenyl, n-hexylphenyl, tert-octylphenyl, isononylphenyl or n-dodecylphenyl.

$R_2$ and $R_3$ may be identical or different and are preferably identical. $R_5$ and $R_6$ are also preferably identical. Also preferred are compounds of formula I, wherein —$NR_2R_3$ and —$NR_5R_6$ are identical.

$R_2$ and $R_3$ as alkyl of 1 to 18 carbon atoms may be typically methyl, ethyl, n-propyl, isopropyl, n-butyl, isobutyl, n-pentyl, n-hexyl, n-heptyl, n-octyl, 2-ethylhexyl, nonyl, decyl, undecyl, dodecyl, heptadecyl or octadecyl.

—$NR_2R_3$ and —$NR_5R_6$ are typically N,N-diisobutyl, N,N-di-n-hexyl, N,N-di-tert-octyl, N,N-di-2-ethylhexyl, N,N-didodecyl, N-methyl-N-phenyl or N-dodecyl-N-phenylradicals.

Where $R_2$ and $R_3$, together with the linking N-atom, form a 5- to 7-membered heterocyclic ring which may additionally contain a further N- or O-atom, said ring is preferably a saturated ring, preferably a 6-membered ring. Such a ring is typically the piperidine, hexamethyleneimine, piperazine or morpholine ring.

$R_4$ may be alkylene of 1 to 12 carbon atoms, typically methylene, ethylene, trimethylene, 2,2-dimethyl-1,3-propanediyl, tetramethylene, pentamethylene, hexamethylene, heptamethylene, octamethylene, decamethylene or dodecamethylene. Trimethylene, tetramethylene, hexamethylene and octamethylene are preferred.

$R_4$ as alkylene which is interrupted by oxygen atoms, preferably by 1 or 2 oxygen atoms, may be 3-oxapentane-1,5-diyl; 3,6-dioxaoctane-1,8-diyl; 2-oxapropane-1,3-diyl; 2,7-dioxaoctane-1,8-diyl or 2,6-dioxa-4,4-dimethydiyl-1,7-heptanediyl.

$R_4$ as alkenylene of 2 to 12 carbon atoms may contain one or more double bonds, preferably one double bond, and be straight-chain or branched. Illustrative examples of such alkenyl radicals are: vinylene, alkylene, 2-methalkylene, 2-hexenylene, 2-methyl-3-butenylene, 4-propyl-2-pentenylene, 2-decenylene or dodecenylene.

$R_4$ as alkenylene which is interrupted by 1 or 2 oxygen atoms may be 3-oxa-5-heptenylene, 2,7-dioxa-4-octenylene, 3,8-dioxa-5-decenylene or 3-oxa-5,8-undecadienylene.

Preferred compositions are those which contain at least one compound of formula I, wherein $R_1$ is alkyl of 1 to 18 carbon atoms, an unsubstituted cycloalkyl group of 5 to 8 carbon atoms, phenyl, $C_7$–$C_{12}$alkylphenyl, —$NR_5R_6$ or $C_7$–$C_{12}$phenylalkyl, $R_2$ and $R_3$ and $R_5$ and $R_6$ are identical or different and are each alkyl of 1 to 18 carbon atoms or phenyl, or $R_2$ and $R_3$, and $R_5$ and $R_6$ respectively, together with the linking N-atom, form a piperidino, hexamethyleneimino, piperazino or morpholino group, and $R_4$ is alkylene of 1 to 12 carbon atoms or alkenylene of 2 to 12 carbon atoms.

It is within the scope of this invention that any mixture of several compounds of formula I may be used in the novel compositions.

Particularly preferred compositions are those which contain the compounds of formula I, wherein $R_1$ is alkyl of 1 to 18 carbon atoms, phenyl, —$NR_5R_6$ or benzyl, preferably alkyl of 6 to 18 carbon atoms, —$NR_5R_6$ or phenyl, and $R_2$ and $R_3$ and $R_5$ and $R_6$ are identical or different and are alkyl of 1 to 18 carbon atoms, preferably alkyl of 1 to 12 carbon atoms, and $R_4$ is alkylene of 2 to 10 carbon atoms.

Further particularly preferred compositions are those which contain at least one compound of formula I, wherein $R_2$ and $R_3$ are each independently of the other alkyl of 4 to 8 carbon atoms and $R_4$ is alkylene of 1 to 10 carbon atoms or alkenylene of 2 to 10 carbon atoms, but is preferably alkylene of 3 to 8 carbon atoms.

Very particularly preferred compositions are those which contain at least one compound of formula I, wherein $R_1$ is phenyl or —$NR_5R_6$, and $R_2$ and $R_3$ and $R_5$ and $R_6$ are each independently of the other alkyl of 1 to 8 carbon atoms.

Further very particularly preferred compositions are those which contain at least one compound of formula I, wherein when x is 1, $R_1$ is phenyl or —$NR_5R_6$ and $R_2$ and $R_3$ and $R_5$ and $R_6$ are identical and are each alkyl of 1 to 12 carbon atoms, or wherein, when x is 2, $R_4$ is alkylene of 3 to 8 carbon atoms and $R_2$ and $R_3$ are each alkyl of 3 to 10 carbon atoms.

Yet further very particularly preferred compounds are those which contain at least one compound of formula I, wherein when x is 1, $R_1$ is phenyl and $R_2$ and $R_3$ are identical and are each ethyl, propyl, n-butyl, isobutyl, hexyl or 2-ethylhexyl, or wherein, when x is 2, $R_4$ is tetramethylene and $R_2$ and $R_3$ are each 2-ethylhexyl.

Some of the compounds of formula I are known from the publications cited below or can be prepared by methods which are known per se.

Such methods are described in L. Beyer et al., Journal für praktische Chemie, Vol. 317, No. 5, 1975, pp. 829–939; H. Hartmann et al., Journal für praktische Chemie, Vol. 315, No. 1, 1973, pp. 144–148, and in K.-H. König et al., Chemische Berichte 120, pp. 1251–1253, (1987).

In analogy to the per se known methods, the ligands in the compounds of formula I (compounds of formula I without Cu) can be prepared by the following general equations:

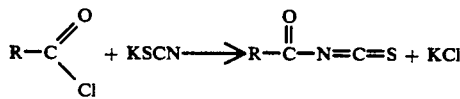

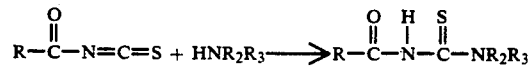

or

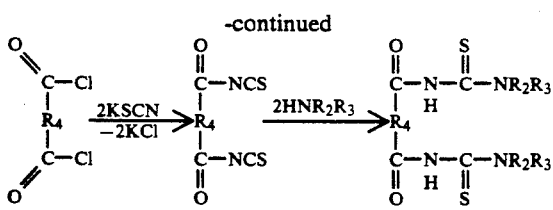

The ligands of compounds of formula I, in which $R_1$ is $-NR_5R_6$, can be prepared in accordance with the following reaction scheme:

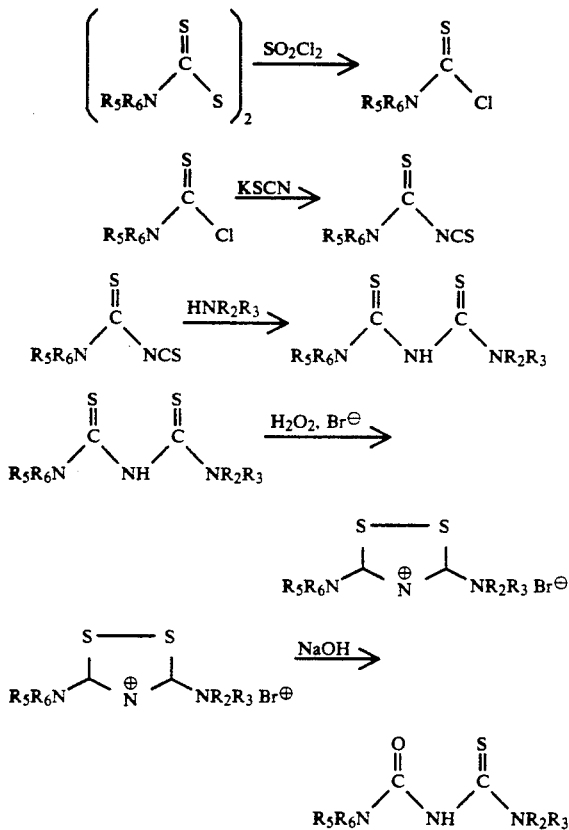

Reference is also made in this connection to A. N. Pudovik et al., Zh. Obshch. Khim., Vol. 58, No. 7, 1988, S. 1489–1493; J. E. Oliver et al., J. Medicinal Chem., Vol. 15, No. 3, 1972, pp. 315–320.

The symbols $R_1$, $R_2$, $R_3$, $R_4$, $R_5$ and $R_6$ have the meanings given hereinbefore.

The starting materials, for example an acyl chloride, a thiocyanate and the chosen amine, may be reacted in a polar aprotic solvent in the temperature range from ca. 50° to 70° C.

Suitable acyl chlorides can be derived by analogy from the foregoing definitions of $R_1$ and are typically acetyl chloride, butyryl chloride, oleolyl chloride, 3-phenylpropionyl chloride, benzoyl chloride or, for $R_4$, glutaryl dichloride, adipyl dichloride, suberyl dichloride, sebacyl dichloride, and the like.

Suitable thiocyanates are typically ammonium thiocyanate, sodium thiocyanate and, preferably, potassium thiocyanate.

In accordance with the meanings of $R_2$ and $R_3$, suitable amines are n-butylamine, 2-ethylhexylamine, dihexylamine, bis(2-ethylhexyl)amine, methyl aniline, piperdine, hexamethyleneimine, morpholine, pyrrolidine or piperazine.

The starting materials referred to above are cited by way of example. The complete starting materials may be inferred by analogy from all substituents suitable for R, $R_2$ and $R_3$.

The compounds of formula I can be readily prepared via the complexing of the sulfur-nitrogen ligands with copper (II) salts at elevated temperature, for example at 50°–60° C., in a solvent such as methanol, ethanol, toluene or xylene. The reactions are almost quantitative, and the complexes can be easily purified by crystallisation.

The compositions of this invention comprise, as further component, a lubricant or a hydraulic fluid. The per se known products can be used as lubricants.

The desired properties of the compounds of this invention are also fully present in the hydraulic fluids, even though in this case the low ash and phosphorus content or freedom from ash and phosphorus does not have the significance mentioned above.

The suitable lubricants and hydraulic fluids are known to the skilled person and are described, for example, in Dieter Klamann "Schmierstoffe und verwandte Produkte" (Lubricants and Related Products), Verlag Chemie, Weinheim, 1982, in Schewe-Kobek, "Das Schmiermittel-Taschenbuch" (The Lubricant Handbook), Dr. Alfred Hüthig-Verlag, Heidelberg, 1974, or in "Ullmanns Encyclopädie der technischen Chemie" (Ullmann's Encyclopedia of Industrial Chemistry), Vol. 13, pages 85–94 (Verlag Chemie, Weinheim, 1977).

Exemplary of lubricants and hydraulic fluids are those derived from mineral oils or mixtures of mineral and synthetic oils, or synthetic lubricants or hydraulic fluids, such as those which are carboxylic acid derivatives and are used at temperatures of 200° C. and above.

Synthetic lubricants typically comprise also lubricants derived from a diester of a dibasic acid with a monohydric alcohol, typically dioctyl sebacate or dinonyl adipate, of a triester of trimethylolpropane with a monobasic acid or with a mixture of such acids, for example trimethylolpropane tripelargonate, trimethylolpropane tricaprylate or mixtures thereof, of a tetraester of pentaerythritol with a monobasic acid or with a mixture of such acids, such as pentaerythritol tetracaprylate, or of a complex ester of monobasic and dibasic acids with polyhydric alcohols, such as a complex ester of trimethylolpropane with caprylic and sebacic acid or of a mixture thereof.

Particularly suitable lubricants are, in addition to mineral oils, typically poly-α-olefins, ester-based lubricants, phosphates, glycols, polyglycols and polyalkylene glycols, and mixtures thereof with water.

The compounds of formula I are readily soluble in lubricants and hydraulic fluids and are therefore especially suitable for use as additives for lubricants and hydraulic fluids. Attention is drawn to their surprisingly good oxidation-inhibiting action.

For example, in lubricants for internal combustion engines, as in the Otto-cycle combustion engine, the outstanding properties of the compounds of formula I are fully effective. Thus the compounds of formula I have an oxidation-inhibiting action in the lubricant oil without adversely affecting a catalytic exhaust gas purification system.

Even when used in very minor amounts, the compounds of formula I act as additives in lubricants and hydraulic fluids. They are conveniently added to the lubricants and hydraulic fluids in an amount of 0.01 to 5% by weight, preferably 0.05 to 3% by weight and, most preferably, 0.1 to 2% by weight, based in each case on the lubricant or the hydraulic fluid.

The compounds of formula I have a very special action when used together with aromatic amines and/or alkali metal dithiophosphates.

Accordingly, the present invention also relates to a composition comprising
a) a lubricant or a hydraulic fluid,
b) at least one compound of formula I

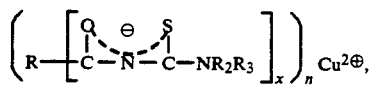

wherein R, $R_2$ and $R_3$ are as defined above, and
c) at least one aromatic amine and/or at least one alkali metal dithiophosphate.

The aromatic compound is preferably a compound of formulae II, III or a mixture of such compounds

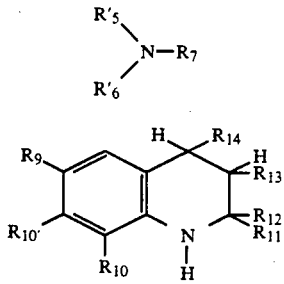

wherein
$R'_5$ is $C_1-C_{18}$alkyl, $C_7-C_9$phenylalkyl, $C_5-C_{12}$cycloalkyl, phenyl, $C_7-C_{18}$alkylphenyl, $C_7-C_{18}$alkoxyphenyl or naphthyl,
$R'_6$ is phenyl, $C_7-C_{18}$alkylphenyl, $C_7-C_{18}$alkoxyphenyl or naphthyl,
$R_7$ is hydrogen, $C_1-C_{12}$alkyl, benzyl, allyl, methallyl, phenyl, or a group $-CH_2SR_8$, and
$R_8$ is $C_4-C_{18}$alkyl, $-CH_2COO(C_4-C_{18}$alkyl) or $-CH_2CH_2COO(C_4-C_{18}$alkyl), and
$R_9$ and $R_{10}$ are each independently of the other hydrogen, $C_1-C_{18}$alkyl or benzyl, and
$R_{10'}$ is hydrogen or $C_1-C_{12}$alkyl or, when taken together with $R_{10}$, forms a butadienediyl radical, and
$R_{11}$ and $R_{12}$ are each independently of the other $C_1-C_{18}$alkyl, phenyl or benzyl, or $R_{11}$ and
$R_{12}$, together with the linking carbon atom, form a $C_5-C_{12}$spirocycloalkyl ring, and
$R_{13}$ is hydrogen or $C_1-C_{18}$alkyl, and
$R_{14}$ is $C_1-C_{18}$alkyl, or
$R_{13}$ and $R_{14}$, together with both linking carbon atoms, are a $C_5-C_{12}$cycloaliphatic radical.

Preferred compounds of formula II are those wherein
$R'_5$ is $C_1-C_4$alkyl, $C_7-C_9$phenylalkyl, cyclohexyl, phenyl, $C_{10}-C_{18}$alkylphenyl or naphthyl,
$R'_6$ is $C_{10}-C_{18}$alkylphenyl or phenyl,
$R_7$ is hydrogen, $C_1-C_8$alkyl, benzyl, allyl or a group $-CH_2SR_8$,
$R_8$ is $C_8-C_{18}$alkyl or $-CH_2COO(C_8-C_{18}$alkyl), and especially those wherein $R'_5$ and $R'_6$ are each independently of the other phenyl or $C_{10}-C_{18}$alkylphenyl and $R_7$ is hydrogen.

Most preferably the compound of formula II is a technical mixture obtained by reacting diphenylamine with diisobutylene as described in U.S. Pat. No. 4,824,601, said mixture comprising
1 to 5% by weight of a) diphenylamine
8 to 18% by weight of b) 4-tert-butyldiphenylamine
21 to 31% by weight of c) one or more of the compounds selected from
i) 4-tert-octyldiphenylamine
ii) 4,4'-di-tert-butyldiphenylamine
iii) 2,4,4'-tris-tert-butyldiphenylamine,
20 to 31% by weight of d) one of more of the compounds selected from
i) 4-tert-butyl-4'-tert-octyldiphenylamine
ii) 2,2'- or 2,4'-di-tert-octyldiphenylamine
iii) 2,4-di-tert-butyl-4'-tert-octyldiphenylamine and
15 to 29% by weight of e) the compound
i) 4,4'-di-tert-octyldiphenylamine or of the compounds
i) 4,4'-di-tert-octyldiphenylamine and
ii) 2,4-di-tert-octyl-4'-tert-butyldiphenylamine;
preferably a mixture comprising
a) 3% of diphenylamine,
b) 14% of 4-tert-butyldiphenylamine,
c) 30% of 4-tert-octyldiphenylamine, 4,4'-di-tert-butyldiphenylamine and 2,4,4'-tris-tert-butyldiphenylamine,
d) 29% of 4-tert-butyl-4'-tert-octyldiphenylamine, 2,2'- and 3,3'-di-tert-octyldiphenylamine and 2,4-di-tert-butyl-4'-tert-octyldiphenylamine,
e) 18% of 4,4'-di-tert-octyldiphenylamine,
f) 6% of 2,4-di-tert-octyl-4'-tert-butyldiphenylamine.

Preferred compounds of formula III are those wherein $R_9$ and $R_{10}$ are each independently of the other hydrogen or $C_1-C_{12}$alkyl, and $R_{10'}$ is hydrogen or, when taken together with $R_{10}$, forms a butadiendiyl radical, and $R_{11}$ and $R_{12}$ are each independently of the other $C_1-C_{12}$alkyl, or $R_{11}$ and $R_{12}$, together with the linking carbon atom, form a $C_5-C_7$spirocycloalkyl ring, and $R_{13}$ is hydrogen and $R_{14}$ is $C_1-C_{12}$alkyl, or $R_{13}$ and $R_{14}$, together with both linking carbon atoms, form a cyclohexane radical; but are preferably those wherein $R_9$ is hydrogen or $C_1-C_{12}$alkyl, $R_{10}$ is hydrogen, methyl or ethyl, $R_{10'}$ is hydrogen or, when taken together with $R_{10}$, forms a butadienediyl radical, and $R_{11}$ and $R_{12}$ are methyl or ethyl, or $R_{11}$ and $R_{12}$, together with the linking carbon atom, form a spirocyclohexyl ring, and $R_{13}$ is hydrogen and $R_{14}$ is methyl or ethyl.

The most preferred compound of formula III is 2,2,4-trimethyl-1,2,3,4-tetrahydroquinoline.

The compounds of formula III are prepared by methods which are known per se and described, for example, in U.S. Pat. No. 4,692,258.

Preferred alkali metal dithiophosphates have the formula IV

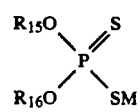

wherein $R_{15}$ and $R_{16}$ are each independently of the other $C_1-C_{24}$alkyl or $C_2-C_{12}$alkyl which is interrupted by $-O-$, $-S-$ and/or $-C(O)O-$: unsubstituted or $C_1-C_{12}$alkyl-substituted phenyl; $C_5-C_{12}$cycloalkyl or $C_5-C_{12}$cycloalkyl which is substituted by $C_1-C_4$alkyl;

or is $C_7$-$C_{13}$phenylalkyl or $C_7$-$C_{13}$phenylalkyl which is interrupted in the alkyl moiety by —O— or —S—, or $R_{15}$ and $R_{16}$, when taken together, are a dimethylene or trimethylene group or a dimethylene or trimethylene group which is substituted by $C_1$-$C_4$alkyl, and wherein M is an alkali metal. Particularly interesting alkali metal dithiophosphates, however, are those wherein $R_{15}$ and $R_{16}$ are each independently of the other $C_3$-$C_8$alkyl or $C_8$-$C_{12}$alkyl-substituted phenyl, and M is Na or K.

$R_{15}$ and $R_{16}$ as $C_1$-$C_{24}$alkyl are straight-chain or branched alkyl radicals such as methyl, ethyl, n-propyl, isopropyl, n-butyl, isobutyl, sec-butyl, tert-butyl, 2-methylpropyl, pentyl, hexyl, heptyl, octyl, 2-ethylhexyl, nonyl, decyl, undecyl, dodecyl, tetradecyl, hexadecyl, heptadecyl, octadecyl or icosyl. Radicals of 3 to 12 carbon atoms are preferred and radicals of 3 to 8 carbon atoms are particularly preferred.

When $R_{15}$ and $R_{16}$ are $C_2$-$C_{12}$alkyl which is interrupted by —O—, —S— or —C(O)O—, the hetero atom or the C(O)O— group may be in any position, and the $C_2$-$C_{12}$alkyl radical can be interrupted by one or more identical or different hetero atoms as well as by C(O)O— groups, preferably by one such hetero atom or group.

$R_{15}$ and $R_{16}$ as $C_1$-$C_{12}$alkyl-substituted phenyl may be substituted in the phenyl moiety by one or more alkyl groups, but preferably by one or two alkyl groups. $C_1$-$C_{12}$Alkyl is typically methyl, ethyl, n-propyl, isopropyl, n-butyl, isobutyl, sec.butyl, tert-butyl, straight-chain or branched nonyl or dodecyl. Monosubstituted phenyl is preferred, the alkyl substituent preferably containing 3 to 12, most preferably 8 12, carbon atoms. Nonylphenyl is especially preferred.

$R_{15}$ and $R_{16}$ as $C_5$-$C_{12}$cycloalkyl are typically cyclopentyl, cyclohexyl, cycloheptyl, cyclooctyl, cyclononyl, cyclodecyl, cycloundecyl or cyclododecyl. Cyclohexyl is preferred.

$R_{15}$ and $R_{16}$ as $C_1$-$C_4$alkyl-substituted $C_5$-$C_{12}$cycloalkyl may carry one or more substituents, preferably one substituent. Illustrative examples are methylcyclohexyl, trimethylcyclohexyl, butylcyclohexyl or propylcyclopentyl.

$R_{15}$ and $R_{16}$ as $C_7$-$C_{13}$aralkyl may be benzyl, 1- or 2-phenylethyl, 3-phenylpropyl, α, α-dimethylbenzyl, 2-phenylisopropyl, 2-phenylhexyl, benzhydryl or naphthylmethyl. Benzyl is preferred.

$R_{15}$ and $R_{16}$ $C_7$-$C_{13}$aralkyl which is interrupted in the alkyl moiety by —O— or —S— is typically a phenoxyethyl group.

Where $R_{15}$ and $R_{16}$ together are a dimethylene or trimethylene group which is substituted by $C_1$-$C_4$alkyl, the dimethylene or trimethylene group preferably carries one, two or three alkyl groups of 1, 2, 3 or 4 carbon atoms and, most preferably, one or two alkyl groups of 1, 2 or 4 carbon atoms.

M is an alkali metal such as Li, Na, K or Rb. Preferred metals M are Na and K, most preferably Na.

Compounds of formula IV, wherein $R_{15}$ and $R_{16}$ are each independently of the other 2-methylpropyl or 2-ethylhexyl, are very particularly preferred.

Most preferably, the compounds of formula IV are sodium O,O-bis(2-methylpropyl)dithiophosphate or sodium O,O-bis(2-ethylhexyl)dithiophosphate.

These compounds of formulae II, III and/or IV are added to the compositions of the invention conveniently in an amount of 0.01 to 5% by weight, preferably 0.05 to 3% by weight and, most preferably, 0.1 to 2% by weight, in each case based on the weight of the lubricant or hydraulic fluid, with the proviso that the addition of the compounds of formula I, II, III and/or IV does not exceed a total amount of 5% by weight, based on said lubricant or hydraulic fluid.

The compounds of formula I on the one hand, and the compounds of formula II, III and/or IV on the other, are conveniently added in about equal proportions by weight.

Accordingly, the present invention relates also to a method of stabilising lubricant compositions or hydraulic fluids against oxidative or thermal degradation, which comprises adding at least one compound of formula I by itself or together with at least one aromatic amine and/or at least one alkali metal dithiophosphate.

The lubricant compositions and hydraulic fluids of this invention may also contain other additives which are added for further enhancement of the basic properties of said fluids. Such additional additives comprise antioxidants, metal deactivators, rust inhibitors, viscosity index improvers, pour-point depressants, dispersants, detergents and other antiwear additives. Illustrative examples of these additives are:

1. Alkylated monophenols
2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, o-tert-butylphenol.

2. Alkylated hydroquinones
2,6-di-tert-butyl-4-methoxyphenol, 2,5-di-tert-butylhydroquinone, 2,5-di-tert-amylhydroquinone, 2,6-diphenyl-4-octadecyloxyphenol.

3. Hydroxylated thiodiphenyl ethers
2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

4. Alkylidenebisphenols
2,2'-methylenebis(6-tert-butyl-4-methylphenol), 2,2'-methylenebis(6-tert-butyl-4-ethylphenol), 2,2'-methylenebis[4-methyl-6-(α-methylcyclohexy)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol),4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl]terephthalate.

5. Benzyl compounds
1,3,5-tris(3,5-di-tert-butyl-4-hydroxybenzyl)-2,4,6-trimethylbenzene, bis(3,5-di-tert-butyl-4-hydroxybenzyl)sulfide, isooctyl 3,5-di-tert-butyl-4-hydroxybenzylmercaptoacetate, bis(4-tert-butyl-3-hydroxy-2,6-dimethylbenzyl)dithiolterephthalate, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

6. Acylaminophenols 4-hydroxylauranilide, 4-hydroxystearanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

7. Esters of β-(3,5-di-tert-butyl-4-hydroxyphenyl)-propionic acid with mono- or polyhydric alcohols, e.g. with methanol, diethylene glycol, octadecanol, 1,6-hexanediol, neopentyl glycol, triethylene glycol, penetaerythritol, tris(hydroxyethyl)isocyanurate, thiodiethylene glycol, bis(hydroxyethyl)oxalodiamide.

8. Esters of β-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopenthyl glycol, tris(hydroxyethyl)isocyanurate, thiodiethylene glycol, N,N'-bis(hydroxyethyl)oxalodiamide.

9. Amides of β-(3,5-di-tert-butyl-4-hydroxyphenyl)-propionic acid e.g. N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)-hydrazine.

Examples of amine antioxidants:

N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(naphthyl-2)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethyphenol, 2,4'-diaminodiphenylmethane, 4,4'-diaminodiphenylmethane, N,N,N',N'-tetramethyl-4,4'-diaminodiphenylmethane, 1,2-bis[(2-methyphenyl)amino]ethane, 1,2-bis(-phenylamino)propane, (o-tolyl)biguanide, bis[4-(1',3'-dimethylbutyl)phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothizine.

Examples of further antioxidants:

Aliphatic or aromatic phosphites, esters of thiodipropionic acid or of thiodiacetic acid, or salts of dithiocarbamic or dithiophosphoric acid.

Examples of metal deactivators, for example for copper, are:

triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidene propylenediamine, salicylaminoguanidine and the salts thereof.

Examples of rust inhibitors are:

a) organic acids and the esters, metal salts and anhydrides thereof, for example:

N-oleoyl sarcosine, sorbitan monooleate, lead naphthenate, alkenylsuccinic anhydride, for example dodecenylsuccinic anhydride, alkenylsuccinic partial esters and partial amides, 4-nonylphenoxyacetic acid.

b) Nitrogen-containing compounds, for example:

I. Primary, secondary or tertiary aliphatic or cycloaliphatic amines and amine salts of organic and inorganic acids, for example oil-soluble alkylammonium carboxylates.

II. Heterocyclic compounds, for example:

substituted imidazolines and oxazolines.

c) Phosphorus-containing compounds, for example:

amine salts of phosphoric acid partial esters or phosphonic acid partial esters, zinc dialkyldithiophosphates.

d) Sulfur-containing compounds, for example:

barium dinonylnaphthalene sulfonates, calcium petroleum sulfonates.

Examples of viscosity index improvers are:

polyacrylates, polymethacrylates, vinyl pyrrolidone/methacrylate copolymers, polyvinylpyrrolidones, polybutenes, olefin copolymers, styrene/acrylate copolymers, polyethers.

Examples of pour-point depressants are:

polymethacrylates, alkylated naphthalene derivatives.

Examples of dispersants/surfactants are:

polybutenylsuccinamides or -imides, polybutenylphosphonic acid derivatives, basic magnesium, calcium, and barium sulfonates and phenolates.

Examples of antiwear additives are:

sulfur and/or phosphorus and/or halogen-containing compounds such as sulfonated vegetable oils, zinc dialkyl dithiophosphates, tritolylphosphate, chlorinated paraffins, alkyl and aryldi- and trisulfides, triphenylphosphorothionates, diethanolaminomethyltolyltriazole, bis(2-ethylhexyl)aminomethyltolyltriazole, ethyl 3-[(bisisopropyloxyphosphinothioyl)thio]propionate, mixtures of alkylphenylphosphorothioates, triphenylthiophosphate (triphenylphosphorothioate), the dodecylamine salt of 3-hydroxy-1,3-thiaphosphetan 3-oxide, trithiophosphoric acid 5,5,5-tris[(isooctyl-2-acetate)], 1-[N,N-bis(2-ethylhexyl)aminomethyl-2-mercapto-1H-1,3-benzthiazole.

Some of the compounds of formula I are known, as previously stated above. The compounds of formula I, wherein $R_1$ is $-NR_5R_6$, are novel.

The present invention therefore also relates to compounds of formula I, wherein X is 1, and n is 2 and R and $R_1$ are $-NR_5R_6$, where $R_5$ and $R_6$ as well as $R_2$ and $R_3$ are as defined for formula I.

In preferred novel compounds of formula I, $R_2$ and $R_3$ on the one hand, and $R_5$ and $R_6$ on the other, are identical. Also preferred are those compounds in which $-NR_2R_3$ and $-N_5R_6$ are identical.

In preferred novel compounds of formula I, $R_2$, $R_3$, $R_5$ and $R_6$, which may be identical or different, are $C_1$–$C_{12}$alkyl.

The invention is illustrated in more detail by the following Examples in which, unless otherwise stated, all parts and percentages are by weight.

EXAMPLE 1

A saturated solution of 4.0 g (0.02 mol) of copper(II) acetate monohydrate in 150 ml of methanol is added dropwise at 50° C. to a solution of 9.74 g (0.04 mol) of 1,1-diethyl-3-benzoylthiourea in 600 ml of methanol.

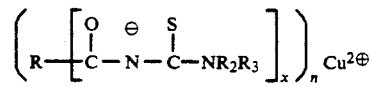

TABLE 1

| Ex. | x | n | R | NR$_2$R$_3$ | m.p. [°C.] | Yield [% d. Th.] | Aspect | Analysis $\begin{bmatrix} \text{calculated} \\ \text{found} \end{bmatrix} \%$ | | | | |
|---|---|---|---|---|---|---|---|---|---|---|---|---|
| | | | | | | | | C | H | N | S | Cu |
| 2 | 1 | 2 | phenyl | —N(C$_3$H$_7$)$_2$ | 107–108 | 99 | greenish-black crystals | 56.21 56.78 | 7.07 6.52 | 9.37 9.25 | 10.72 11.02 | 10.62 10.80 |
| 3 | 1 | 2 | phenyl | —N(C$_4$H$_9$)$_2$ | 95–97 | 92 | black powder | 59.46 59.36 | 7.17 7.17 | 8.67 8.61 | 9.92 10.05 | 9.83 9.90 |
| 4 | 1 | 2 | phenyl | —N(i-C$_4$H$_9$)$_2$ | 158–159 | 94 | black powder | 59.46 59.46 | 7.17 7.14 | 8.67 8.63 | 9.92 9.92 | 9.83 10.0 |
| 5 | 1 | 2 | phenyl | —N(C$_6$H$_{13}$)$_2$ | — | 99 | viscous black oil | 63.33 64.80 | 8.24 8.16 | 7.39 7.08 | 8.45 8.00 | 8.38 7.65 |
| 6 | 1 | 2 | phenyl | —N(2-ethylhexyl)$_2$ | — | 46 | viscous dark brown oil | 66.20 68.75 | 9.03 9.21 | 6.43 5.84 | 7.6 6.98 | 7.30 6.18 |
| 7 | 2 | 1 | ⁅CH$_2$⁆$_4$ | —N(2-ethylhexyl)$_2$ | — | 75 | greenish highly viscous oil | 62.17 62.63 | 9.91 9.75 | 7.25 6.84 | 8.30 8.38 | 8.22 7.88 |

The dark green reaction mixture is stirred for 3 hours at 50°–60° C. and concentrated to ca. ⅓ of its volume. After cooling to 4° C., glistening olive-black crystals of formula

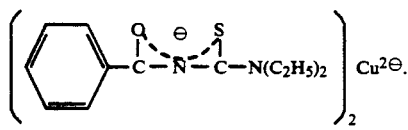

form. Yield: 9.5 g (88.8% of theory) which melt at 102° C.

| Analysis C$_{24}$H$_{30}$N$_4$O$_2$S$_2$Cu: | | | | | |
|---|---|---|---|---|---|
| | C | H | N | S | Cu |
| cal. % | 53.96 | 5.66 | 10.49 | 12.00 | 11.90 |
| found % | 53.98 | 5.70 | 10.49 | 11.91 | 12.0 |

EXAMPLES 2–7:

The compounds listed in Table 1 are prepared in accordance with the general procedure described in Example 1.

EXAMPLE 8

18.9 ml (31.5 g, 0.23 mol) of sulfuryl chloride are added dropwise at 40° C. over 50 minutes to a solution of 119 g (0.29 mol) of tetrabutylthiuram disulfide (MERAMID TBTD) in 400 ml of toluene. The suspension is stirred for 4 hours at 60° C., cooled, filtered, and the filtrate is concentrated by evaporation. For purification, the heterogeneous crude product is taken up in 400 ml of hexane and the solution is filtered and concentrated by evaporation, giving 120 g of a pale brown oil which is distilled at 105°–112° C. and 0.01 torr. Yield: 66 g of dibutylthiocarbamyl chloride (55% of theory) in the form of a pale brown oil of formula

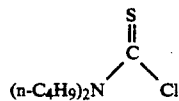

To a solution of 20.8 g (0.1 mol) of dibutylthiocarbamyl chloride in 90 ml of acetone are added 9.7 g (0.1 mol) of potassium thiocyanate. The suspension is stirred under reflux for 15 minutes, then cooled and filtered. Then 17 ml (12.9 g, 0.1 mol) of dibutylamine are added dropwise to the filtered solutuion at 15°–20° C. over 15 minutes. After stirring for 1 hour at room temperature, 11.4 ml of 48% hydrogen bromide (16.9 g, 0.1 mol) and, over 30 minutes, 11.3 g (0.1 mol) of 30% hydrogen peroxide, are added dropwise. The reaction mixture is then stirred for 1 hour at 10°-15° C. and for 1 hour at room temperature. Finally, 50 ml (0.1 mol) of 2N sodium hydroxide solution are added dropwise to the turbid orange solution over 30 minutes at 20°-30° C. The batch is thereafter stirred for 1 hour at room temperature. The organic phase is separated, washed with 3×100 ml of water (pH 7), dried over sodium sulfate and filtered. The filtrate is concentrated by evaporation, giving 32 g of a dark brown oil. This crude product is purified by chromatography over 200 g of silica gel, giving 10 g of 1,1,5,5-tetrabutyl-2-thiobiuret in the form of a medium viscosity dark orange oil of formula

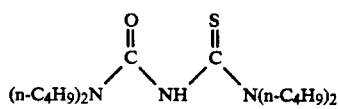

A solution of 0.65 g (2.5 mmol) of copper(II) acetylacetonate in 10 ml of toluene/ethanol (1:1) is added dropwise at 50° C. over 10 minutes to a solution of 1.7 g (5 mmol) of 1,1,5,5-tetrabutyl-2-thiobiuret in 20 ml of toluene/ethanol (1:1). The reaction mixture is filtered after 1 hour and concentrated by evaporation, giving 2.3 g of crude product in the form of a dark, highly viscous oil, which is purified by chromatography over 16 g of silica gel. Yield: 1.0 g of copper complex in the form of a dark green medium viscosity oil (53% of theory) of formula

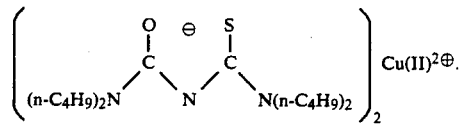

EXAMPLE 9

The procedure of Example 8 is repeated, but starting from tetra(2-ethylhexyl)thiuram disulfide and replacing dibutylamine with bis(2-ethylhexyl)amine, to give the compound of formula

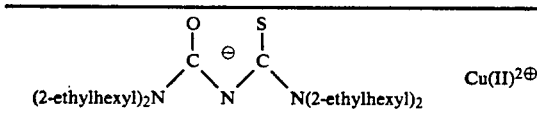

Analytical data:

| Compound of Ex. No. | Aspect | Analyse [calculated found] | | | | |
|---|---|---|---|---|---|---|
| | | C | H | N | S | Cu |
| 8 | dark green medium viscosity oil | 57.60 58.17 | 9.94 9.55 | 11.19 10.97 | 8.54 9.30 | 8.46 8.18 |
| 9 | dark green highly viscous oil | 68.20 69.03 | 11.45 11.22 | 7.02 6.74 | 5.36 5.63 | 5.31 5.07 |

EXAMPLES 10–16:

Thermal stabilisation of a synthetic oil.

The thermal ageing of the formulations is carried out by pressure difference scanning calorimetry (PDSC).

The procedure is carried out as follows: The PDSC cell (Thermoanalysis System 1090, DuPont) consists of a heating block made of silver. A constantan plate, which contains the thermocouples (chromel-alumel) is inserted into this heating block. Specimen pans and reference pans of aluminum are placed on the slightly raised thermoelectric couples. The interior of the DSC cell is coated with a thin gold film (corrosion protection). The reference pan remains empty, while three drops of each formulation are placed in the specimen pan. The difference in temperature between specimen and reference pan under isothermic conditions is determined. The change in enthalpy dH/dt is given in mW. All measurements are carried out in oxygen. The temperature is 180° C. constant. The pressure is 10 bar. The base oil used in each experiment is a commercially available mineral oil (Mobil 150 SSU). To this oil are added 40 ppm of $Fe^{3\oplus}$ to increase the susceptibility of the oil to oxidation. To test the effectiveness, the oil contains the additives listed in Table 2 in the indicated amounts.

During the thermal ageing, the concentration of the additives continually decreases. At a critical additive concentration, the heat of reaction dH7dt increases. The time taken until this rise occurs is termed induction time (onset). Long induction times indicate a high ageing stability of the oils.

The following formulations listed in Table 2 are prepared and measured.

TABLE 2

| Ex. | Additive compound of Ex. | conc. [%] | Oil | Induction time [min] |
|---|---|---|---|---|
| 10 | 3 | 0.5 | base oil | 25.6 |
| 11 | 6 | 0.5 | base oil | 16.2 |
| 12 | 3 + amine-AO* | 0.2 0.3 | base oil | 37.5 |
| 13 | 3 + amine-AO* | 0.1 0.4 | base oil | 50.5 |
| 14 | 6 + amine-AO* | 0.2 0.3 | base oil | 31.7 |
| 15 | 8 + amine-AO* | 0.1 0.4 | base oil | 57 |
| 16 | 9 + amine-AO* | 0.1 0.4 | base oil | 33 |
| — | — | — | base oil | <1 |

*Amine-AO: Technical mixture obtained by reacting diphenylamine with diisobutylene, corresponding to the composition
a) 3% diphenylamine,
b) 14% 4-tert-butyldiphenylamine,
c) 30% 4-tert-octyldiphenylamine, 4,4'-di-tert-butyldiphenylamine and 2,4,4'-tris-tert-butyldiphenylamine,
d) 29% 4-tert-butyl-4'-tert-octyldiphenylamine, 2,2'-and 3,3'-di-tert-octyldiphenylamine, and 2,4-di-tert-butyl-4'-tert-octyldiphenylamine,
e) 18% 4,4'-di-tert-octyldiphenylamine,
f) 6% 2,4-di-tert-octyl-4'-tert-butyldiphenylamine.

EXAMPLE 17

Using the same PDSC method as in Examples 10–16, the induction time is determined of a formulation comprising the compound of Example 3 and sodium O,O-bis(2-ethylhexyl)dithiophosphate (Na-DTP). The results are reported in Table 3.

TABLE 3

| Additive compound of Ex. | Conc. [%] | Oil | Induction time [min] |
|---|---|---|---|
| 3 + Na-DTP | 0.25 0.25 | base oil | 23.6 |
| 3 | 0.5 | base oil | 25.6 |
| Na-DPT | 0.5 | base oil | 5.7 |
| — | — | base oil | <1 |

EXAMPLE 18

The oxidation inhibiting action is determined using an oscillating friction device supplied by Optimol GmbH, Munich.

The procedure is desribed in detail by R. Schumacher, D. Landolt, H. J. Mathieu and H. Zinke, Surface Reaction of Isogeometrical Phosphorus Compounds, ASLE Transaction, 26 (1982) 94–101.

This device operates as follows: A steel ball (100 Cr 6), on which the force $F_N$ is exerted, oscillates on a steel cylinder. The ball is fixed in a holding device and so performs an oscillating slip movement. The horizontal and vertical force is determined by a piezoelectrical transducer. Under the given test conditions, the maximum standard voltage is 2740 N/mm$^2$, and the maximum shearing stress is 850 N/mm$^2$. Ball and cylinder are made of the same tool steel.

A few drops of oil in which the formulation to be tested is dissolved are applied between cylinder and ball. The following test conditions are chosen:

| Test conditions: | |
|---|---|
| load | 50 N |
| temperature | 200° C. |
| frequency | 50 Hz |
| amplitude | 1000 μm |
| time taken | Until the device is switched off because of overloading (oil thickening caused by oxidative degradation). Long duration means a good oxidation inhibiting action. The results are reported in Table 4. |

The base oil used is a low reference oil for diesel engines.

TABLE 4

| Composition | Time taken [h] |
|---|---|
| base oil + 0.2% 3* + 0.3% Na-DTP** | 42 |
| base oil | 35 |

*compound of Example 3
**see Example 17

EXAMPLE 19

In accordance with the procedure of Example 18, the formulation of Example 12 in the same oil is tested.

The time taken until the device is switched off because of overloading caused by oil thickening is 45 hours.

What is claimed is:

1. A composition comprising
   a) a lubricant or a hydraulic fluid, and
   b) an effective stabilizing amount of a compound of formula I

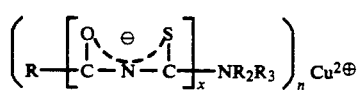

(I)

wherein x is 1 or 2 and, when x is 1, n is 2 and R has the meaning of R$_1$, or, when x is 2, n is 1 and R has the meaning of R$_4$, and R$_1$ is alkyl of 1 to 25 carbon atoms, an unsubstituted or C$_1$-C$_8$-alkyl-substituted cycloalkyl group of 5 to 12 carbon atoms, alkenyl of 2-18 carbon atoms, phenyl, naphthyl, C$_7$-C$_{18}$-phenylalkyl, C$_7$-C$_{18}$alkylphenyl or —NR$_5$R$_6$, and R$_2$ and R$_3$ are identical or different and are alkyl of 1 to 18 carbon atoms, phenyl, naphthyl, C$_7$-C$_{18}$-phenylalkyl or C$_7$-C$_{18}$alkylphenyl, or R$_2$ and R$_3$, together with the linking nitrogen atom, form a 5- to 7-membered heterocyclic ring which may additionally contain a N- or O-atom, R$_4$ is alkylene of 1 to 12 carbon atoms which may be interrupted by at least one —O—group, or is alkenylene of 2 to 12 carbon atoms which may be interrupted by at least one —O—group, and R$_5$ and R$_6$ have the same meanings as R$_2$ and R$_3$.

2. A composition according to claim 1, wherein R$_1$ is alkyl of 1 to 18 carbon atoms, an unsubstituted cycloalkyl group of 5 to 8 carbon atoms, phenyl, C$_7$-C$_{12}$alkylphenyl, —NR$_5$R$_6$ or C$_7$-C$_{12}$phenylalkyl, R$_2$ and R$_3$ and R$_5$ and R$_6$ are identical or different and are each alkyl of 1 to 18 carbon atoms or phenyl, or R$_2$ and R$_3$ and R$_5$ and R$_6$ respectively, together with the linking N-atom, form a piperidino, hexamethyleneimino, piperazino or morpholino group, and R$_4$ is alkylene of 1 to 12 carbon atoms or alkenylene of 2 to 12 carbon atoms.

3. A composition according to claim 1, wherein R$_1$ is alkyl of 1 to 18 carbon atoms, phenyl, —NR$_5$R$_6$ or benzyl, and R$_2$ and R$_3$ and R$_5$ and R$_6$ are identical or different and are each alkyl of 1 to 18 carbon atoms.

4. A composition according to claim 1, wherein R$_1$ is alkyl of 6 to 18 carbon atoms, —NR$_5$R$_6$ or phenyl, and R$_2$ and R$_3$ and R$_5$ and R$_6$ are each independently of the other alkyl of 1 to 12 carbon atoms and R$_4$ is alkylene of 2 to 10 carbon atoms.

5. A composition according to claim 1, wherein R$_1$ is phenyl or —NR$_5$R$_6$, and R$_2$ and R$_3$ and R$_5$ and R$_6$ are each independently of the other alkyl of 1 to 8 carbon atoms.

6. A composition according to claim 1, wherein R$_2$ and R$_3$ are each independently of the other alkyl of 4 to 8 carbon atoms, and R$_4$ is alkylene of 1 to 10 carbon atoms or alkenylene of 2 to 10 carbon atoms.

7. A composition according to claim 2, wherein R$_2$ and R$_3$ are each independently of the other alkyl of 4 to 8 carbon atoms, and R$_4$ is alkylene of 3 to 8 carbon atoms.

8. A composition according to claim 2, wherein, when x is 1, R$_1$ is phenyl or —NR$_5$R$_6$ and R$_2$ and R$_3$ or R$_5$ and R$_6$ are identical and are each alkyl of 1 to 12 carbon atoms; or wherein, when x is 2, R$_4$ is alkylene of 3 to 8 carbon atoms and R$_2$ and R$_3$ are each alkyl of 3 to 10 carbon atoms.

9. A composition according to claim 1, which c) additionally comprises at least one aromatic amine and/or at least one alkali metal dithiophosphate.

10. A composition according to claim 9, wherein the aromatic amine is a compound of formula II or III or a mixture of such compounds

(II)

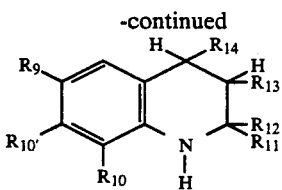 (III)

wherein

R'₅ is $C_1$-$C_{18}$alkyl, $C_7$-$C_9$phenylalkyl, $C_5$-$C_{12}$cycloalkyl, phenyl, $C_7$-$C_{18}$alkylphenyl, $C_7$-$C_{18}$alkoxyphenyl or naphthyl, R'₆ is phenyl, $C_7$-$C_{18}$alkylphenyl, $C_7$-$C_{18}$alkoxyphenyl or naphthyl, R₇ is hydrogen, $C_1$-$C_{12}$alkyl, benzyl, allyl, methallyl, phenyl or a group —CH₂SR₈, and R₈ is $C_4$-$C_{18}$alkyl, —CH₂COO($C_4$-$C_{18}$alkyl) or —CH₂CH₂COO($C_4$-$C_{18}$alkyl), and R₉ and R₁₀ are each independently of the other hydrogen, $C_1$-$C_{18}$alkyl or benzyl, and R₁₀, is hydrogen or $C_1$-$C_{12}$alkyl or, when taken together with R₁₀, forms a butadienediyl radical, and R₁₁ and R₁₂ are each independently of the other $C_1$-$C_{18}$alkyl, phenyl or benzyl, or R₁₁ and R₁₂, together with the linking carbon atom, form a $C_5$-$C_{12}$spirocycloalkyl ring, and R₁₃ is hydrogen or $C_1$-$C_{18}$alkyl, and R₁₄ is $C_1$-$C_{18}$alkyl, or R₁₃ and R₁₄, together with both linking carbon atoms, are a $C_5$-$C_{12}$cycloaliphatic radical.

11. A composition according to claim 10, wherein

R'₅ is $C_1$-$C_4$alkyl, $C_7$-$C_9$phenylalkyl, cyclohexyl, phenyl, $C_{10}$-$C_{18}$alkylphenyl or naphthyl, R'₆ is $C_{10}$-$C_{18}$alkylphenyl or phenyl, R₇ is hydrogen, $C_1$-$C_8$alkyl, benzyl, allyl or a group —CH₂SR₈, R₈ is $C_8$-$C_{18}$alkyl or —CH₂COO($C_8$-$C_{18}$alkyl).

12. A composition according to claim 11, wherein R'₅ and R'₆ are each independently of the other phenyl or $C_{10}$-$C_{18}$alkylphenyl and R₇ is hydrogen.

13. A composition according to claim 12, wherein the compound of formula II is a technical mixture obtained by reacting diphenylamine with diisobutylene, said mixture comprising 1 to 5% by weight of a) diphenylamine
8 to 18% by weight of b) 4-tert-butyldiphenylamine
21 to 31% by weight of c) one or more of the compounds selected from
 i) 4-tert-ocyldiphenylamine
 ii) 4,4'-di-tert-butyldiphenylamine
 iii) 2,4,4'-tris-tert-butyldiphenylamine,
20 to 31% by weight of d) one or more of the compounds selected from
 i) 4-tert-butyl-4'-tert-octyldiphenylamine
 ii) 2,2'- or 2,4'-di-tert-octyldiphenylamine
 iii) 2,4-di-tert-butyl-4'-tert-octyldiphenylamine and
15 to 29% by weight of e) the compound
 i) 4,4'-di-tert-octyldiphenylamine or of the compounds
 i) 4,4'-di-tert-octyldiphenylamine and
 ii) 2,4-di-tert-octyl-4'-tert-butyldiphenylamine;

14. A composition according to claim 10, wherein the aromatic amine is a compound of formula III, wherein R₉ and R₁₀ are each independently of the other hydrogen or $C_1$-$C_{12}$alkyl, and R₁₀' is hydrogen or, when taken together with R₁₀, forms a butadienediyl radical, and R₁₁ and R₁₂ are each independently of the other $C_1$-$C_{12}$alkyl, or R₁₁ and R₁₂, or R₁₁ and R₁₂, together with the linking carbon atom, form a $C_5$-$C_7$spirocycloalkyl ring, and R₁₃ is hydrogen and R₁₄ is $C_1$-$C_{12}$alkyl, or R₁₃ and R₁₄, together with both linking carbon atoms, form a cyclohexane radical.

15. A composition according to claim 14, wherein R₉ is hydrogen or $C_1$-$C_{12}$alkyl, R₁₀ is hydrogen, methyl or ethyl, R₁₀' is hydrogen or, when taken together with R₁₀, forms a butadienediyl radical, and R₁₁ and R₁₂, together with the linking carbon atom, form a spirocyclohexyl ring, and R₁₃ is hydrogen and R₁₄ is methyl or ethyl.

16. A composition according to claim 14, wherein the compound of formula III is 2,2,4-trimethyl-1,2,3,4-tetrahydroquinoline.

17. A composition according to claim 9, wherein the alkali metal dithiophosphate is a compound of formula IV

 (IV)

wherein R₁₅ and R₁₆ are each independently of the other $C_1$-$C_{24}$alkyl or $C_2$-$C_{12}$alkyl which is interrupted by —O—, —S— and/or —C(O)O—; unsubstituted or $C_1$-$C_{12}$alkyl-substituted phenyl; $C_5$-$C_{12}$cycloalkyl or $C_5$-$C_{12}$cycloalkyl which is substituted by $C_1$-$C_4$alkyl; or is $C_7$-$C_{13}$phenylalkyl which is interrupted in the alkyl moiety by —O— or —S—, or R₁₅ and R₁₆, when taken together, are a dimethylene or trimethylene group or a dimethylene or trimethylene group which is substituted by $C_1$-$C_4$alkyl, and wherein M is an alkali metal.

18. A composition according to claim 17, wherein R₁₅ and R₁₆ are each independently of the other $C_3$-$C_8$alkyl or $C_8$-$C_{12}$alkyl-substituted phenyl, and M is Na or K.

19. A composition according to claim 18, wherein R₁₅ and R₁₆ are each independently of the other 2-methylpropyl or 2-ethylhexyl.

20. A composition according to claim 17, wherein the compound of formula IV is sodium O,O-bis(2-methylpropyl)dithiophosphate or sodium O,O-bis(2-ethylhexyl)dithiophosphate.

21. A method of stabilising a lubricant or hydraulic fluid against oxidative and/or thermal degradation, which comprises adding to said lubricant or hydraulic fluid at least one compound of formula I according to claim 1.

22. A method of stabilising a lubricant or hydraulic fluid against oxidative and/or thermal degradation, which comprises adding to said lubricant or hydraulic fluid at least one compound of formula I according to claim 1 and at least one aromatic amine and/or at least one alkali metal dithiophosphate according to claim 9.

* * * * *